United States Patent [19]
Gordon

[11] Patent Number: 4,794,787
[45] Date of Patent: Jan. 3, 1989

[54] HIGH-LOW VISCOSITY COMPARATOR

[76] Inventor: Myron S. Gordon, 1700 Cleveland Rd., Miami Beach, Fla. 33141

[21] Appl. No.: 58,846

[22] Filed: Jun. 5, 1987

[51] Int. Cl.⁴ ............................................. G01N 11/06
[52] U.S. Cl. ............................................. 73/56; 73/64
[58] Field of Search ............................... 73/56, 55, 64

[56] References Cited

U.S. PATENT DOCUMENTS

| | | | |
|---|---|---|---|
| 1,635,281 | 7/1927 | Larson | 73/56 |
| 1,659,534 | 2/1928 | Mason | 73/56 |
| 1,758,677 | 5/1930 | Smith | 73/56 |
| 2,419,658 | 4/1947 | Rogers | 73/55 X |
| 2,823,541 | 2/1958 | Gordon et al. | 73/56 |

FOREIGN PATENT DOCUMENTS 2909373 9/1980 Fed. Rep. of Germany .......... 73/55

*Primary Examiner*—Stewart J. Levy
*Assistant Examiner*—Joseph W. Roskos
*Attorney, Agent, or Firm*—Sherman Levy

[57] ABSTRACT

A method and apparatus is provided for determining decreases and increases of viscosities of used oils or fluids and to detect changes in the oils or fluids during operation in equipment or storage. The limits on both ends can be established by the individual user to meet his or her own specification. Also, the standards can be prepared in a laboratory using various amounts of lesser and higher viscosity oils or fluids to attain the minimum and maximum limits required. There is provided three cups having holes or apertures in the lower end and wherein the holes or apertures are of different sizes, and wherein the cups are adapted to be moved into engagement with containers having oil or fluid therein, and then the cups are raised or immersed to permit the oils or fluids to drain through the holes to accomplish the desired results.

14 Claims, 1 Drawing Sheet

HIGH-LOW VISCOSITY COMPARATOR

BACKGROUND OF THE INVENTION

The present invention generally appertains to improvements in viscosity comparators that are adapted to be used to compare high and low viscosity limits for any type of oil or fluid at any temperature.

DESCRIPTION OF THE PRIOR ART

Viscosity comparatives are well known, as for example as shown in prior U.S. Pat. Nos. 2,823,541; 2,826,060; 4,185,493; 4,426,878; and D187,738. However, neither these prior patents nor any others known to applicant achieve the results accomplished by the present invention.

OBJECTS AND SUMMARY OF THE PRESENT INVENTION

A primary object of the present invention is to provide a multi-functional, modified comparator wherein viscosity of oils or other fluids in the field can be determined, and wherein the present invention provides a quick, simple, and accurate method and apparatus for determining both decreases and increases in viscosities of used oils or fluids and to detect changes in the oils or fluids during operation in equipment or storage.

Another object of the present invention is to provide a method and apparatus for determining decreases and increases in viscosities of used oils or fluids wherein the limits on both ends can be established by the individual user to meet his or her own specification, and wherein the standards can be prepared in a laboratory using various amounts of lesser and higher viscosity oils or liquids to attain the minimum and maximum limits required.

A still further object of the present invention is to provide a method and apparatus of the type described wherein there is provided a comparator which includes a plurality of means that are either immersed in the three samples or oils or fluids or the three oil samples can be raised and wherein a single test conducted on a sample of used oil or fluid can be compared with a sample of new oil to immediately determine if the used oil has been excessively thinned or thickened thus rendering it unfit for further use.

Another object of the present invention is to provide a truly portable viscosity comparator that requires no electricity or electronics and which can be operated by untrained personnel and wherein the limits of oil thinning and thickening can be determined by the individual user, and the holes in the bottom of the cups can be sized accordingly, and wherein the viscosity comparator of the present invention can be used to compare high and low viscosity limits for any type of oil or fluid at any temperature.

Another major object of the present invention is to provide a viscosity comparator that can be inexpensively manufactured and which will accomplish the desired purposes with maximum efficiency.

These and other objects of the present invention will become apparent with reference to the drawings, the Description of the Preferred Embodiment, and the appended claims.

DESCRIPTION OF THE PREFERRED EMBODIMENT

Figure 1:
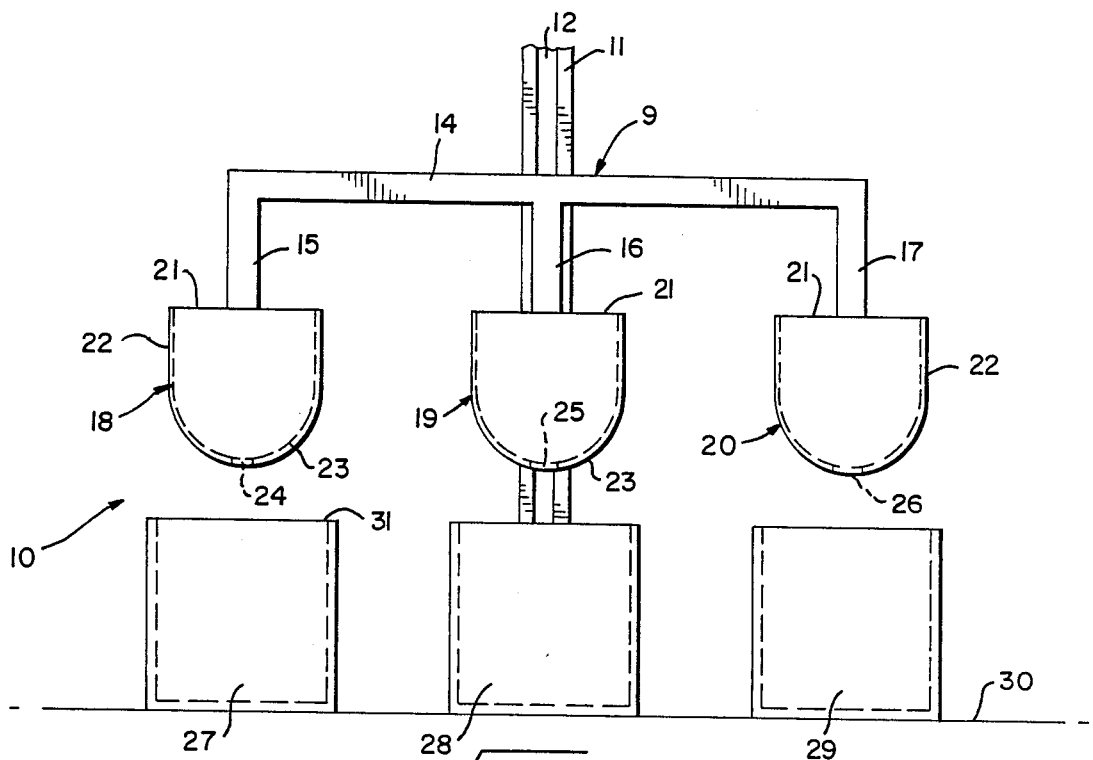
FIG. 1 is a front, elevational view of the viscosity comparator of the present invention.
Figure 2:
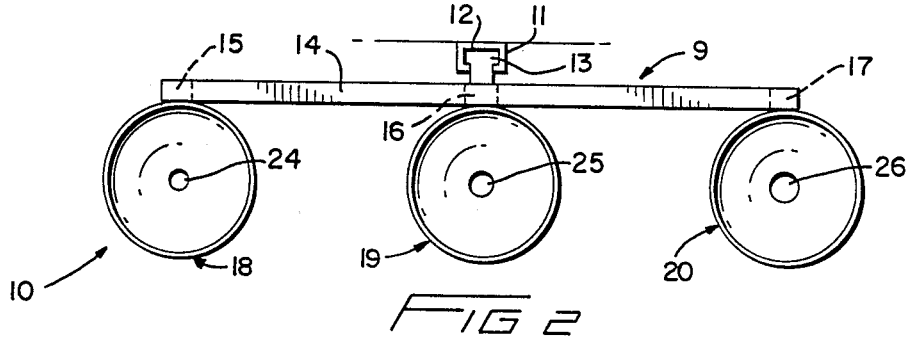
FIG. 2 is a top plan view thereof.

Referring in detail to the drawings, the numeral 10 indicates the viscosity comparator of the present invention which is shown to comprise a vertically disposed support member 11 having a track 12 therein, and a body member 9 includes a vertically disposed portion or rail 13 which is movably or slidably mounted in the track 12, FIG. 2. The body member 9 includes a horizontally disposed cross piece 14 which is secured to or formed integral with the vertical portion 13, and depending from the cross piece 14 are spaced parallel, vertically disposed first, second, and third arms 15, 16, and 17.

There is further provided first, second, and third cups 18, 19, and 20, as shown in the drawings. Each of the cups 18, 19, and 20 has an open upper portion 21 as well as a generally cylindrical upper portion 22 and a curved or rounded bottom portion 23. There is provided in the lower end of the first, second, and third cups 18, 19, and 20 holes or apertures 24, 25, and 26, and these holes 24, 25, and 26 are of different sizes or diameters as shown in the drawings. The size of the hole 25 is greater than the size of the hole 24, and the hole 26 is of greater size or diameter than the hole 25.

Figure 3:
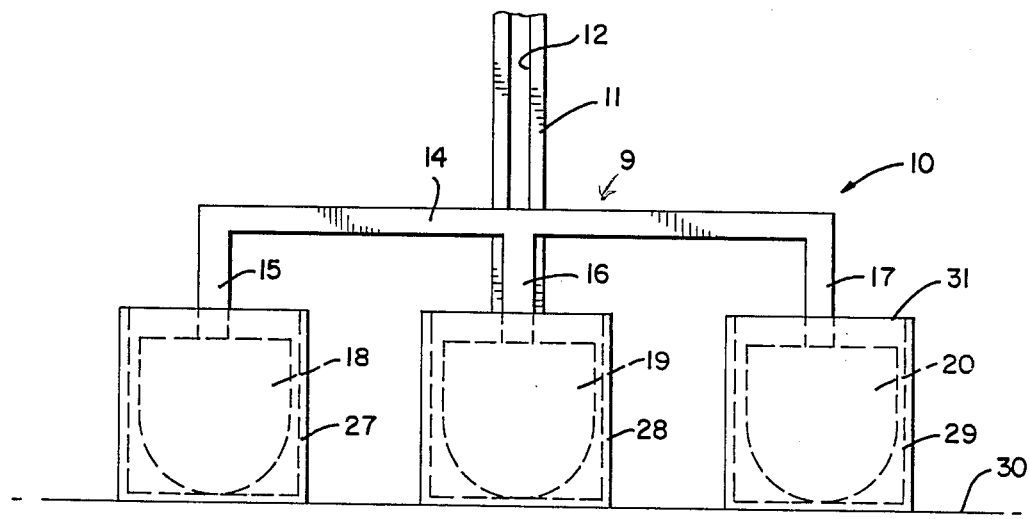
FIG. 3 a front elevational view similar to FIG. 1, but showing the cups in lowered position in the containers or jars containing the oils or fluids.

There is further provided first, second, and third containers or jars 27, 28, and 29 for a purpose to be later described, and the containers or jars 27, 28, and 29 are adapted to be supported on a suitable surface or structure 30. The upper ends of the jar 27, 28, and 29 are open as at 31, and the size or diameter of the jars 27, 28, and 29 are slightly greater than the diameter or size of the cups 18, 19, and 20 so that with the parts in lowered position, as shown in FIG. 3, the cups can fit within the containers 27, 28, and 29.

From the foregoing, it will be seen that there has been provided a viscosity comparator, and it will be understood that the parts can be made of any suitable material and in different shapes or sizes as desired or required.

The present invention provides a method and apparatus for detecting oil thickening or thinning. With reference to prior U.S. Pat. No. 2,823,541, this viscosity comparator consisted of two cups with the same size holes in the bottom, and by comparing the flow of the used oil in one cup with the flow of the sample of the new oil intentionally thinned, it was possible to compare the relative viscosities, i.e., the used oil is more or less thinner than the thinned sample prepared.

However, this system became difficult when making comparisons with oils intentionally thickened. It has been found by applicant that the simplest and most accurate method is to adjust the diameter of the holes in the individual cups to correlate with the flow of oils intentionally thinned and thickened.

In accordance with the present invention, three cups 18, 19, and 20 are used as shown in the drawings, with the new oil standard in the center. One cup 18 on the left side is for the used oil with a smaller sized hole 24 in the bottom to detect oil thinning, and the other cup 20 on the right side for the same used oil with a larger sized hole 26 in the bottom to detect oil thickening so that both tests can be conducted with one operation.

It is contemplated that when using the viscosity comparator of the present invention the used oil or fluid will be placed in containers 27 and 29, and the new oil or fluid will be placed in container 28. Upon filling the containers and immersing the cups in the the respective containers to get the oil or fluid into the cups, the degree of thinning or thickening of the used oil or fluid can be observed. Thus, if the oil in cup 19 stops flowing first, the used oil is too thick, while if the oil in cup 18 stops flowing first, the used oil is too thin.

It is to be understood that when using the method and apparatus of the present invention, the containers 27, 28, and 29 or the cups can be raised so that the oil or fluids can enter the cups, whereby when the cups are raised, the oil or fluids can be discharged downwardly through the holes 24, 26, and 26 to accomplish the desired purposes. As shown in FIG. 3, the height of the containers 27, 28, and 29 are slightly greater than the height of the cups so that the oil or fluid can enter the cups through the open top thereof.

The prior patents include U.S. Pat. No. 4,185,493, but this prior patent is adapted to be used for determining viscosities of heated coal-type materials under high temperatures and pressures, utilizing temperature sensors and requires the need for trained technicians.

In prior U.S. Pat. No. 4,065,959, this is a patent that is directed to the determination of viscosities of paints and liquid asphalts under high temperatures utilizing temperatures, volume, and time sensors and a computer readout and requires the need for trained technicians or personnel.

In prior U.S. Pat. No. 4,426,878, there is shown a viscosimeter that is adapted to be used for determining viscous fluids at high temperatures and pressures utilizing electronically conductive fluids and electrodes to measure the flow of fluids and requires the need for trained technicians or personnel.

In the prior U.S. Pat. No. 2,823,541 of M. S. Gordon et al, this prior patent was primarily to permit an accurate determination of oils and fluids that have been diluted, i.e., mixed with oils of lesser viscosities. By diluting new oils with known measured amounts of lesser viscosity oils, a known diluted sample was prepared that could be compared with a sample of a used oil of the same initial viscosity.

Further, because viscosity increase (thickening) has become as important as viscosity decrease (thinning), the need to determine both factors has become extremely important. Unfortunately, it is very difficult to increase the viscosity of oils in the field as the determination of the required amount of higher viscosity oil necessary to obtain a known viscosity increase is almost impossible without the use of laboratory equipment.

In accordance with the present invention, there is provided a quick, simple, and accurate method for determining both decreases and increases in viscosities of used oils or fluids and to detect changes in oil during operation in equipment or storage. Further, the limits on both ends can be established by the individual user to meet his or her own specifications. The standards can be prepared in a laboratory using various amounts of lesser and higher viscosities of oils or fluids to obtain the minimum and maximum limits that are required thereby.

The triple high-low viscosity comparator (three cups) described and illustrated herein is immersed in the three samples of oils as indicated in the containers 27, 28, and 29. Sample one in the container 27 is the used oil or fluid sample, sample two in the container 28 is the new untouched oil or fluid, and sample three in the container 29 is the same used oil or fluid sample as in container 27. The comparator is withdrawn from the three samples of oils, and the fluid is allowed to flow through the holes 24, 25, and 26 in the bottom of the three cups 18, 19, and 20. The hole 25 in the bottom of the center cup 19 (sample two) is increased in size so that the oil flow from the diluted sample (sample one) stops at the same time as the center cup. The diameter of the hole in cup 20 holding the thickened oil or fluid (sample three) is increased in size so that the oil flow from the cup 20 stops at the same time as the oil flow from center cup 19.

In this manner, the various diameters of the holes in the bottoms of the three cups have been sized to predetermine the low and high viscosities acceptable. Now a single test conducted on a sample of used oil can be compared with a sample of new oil to immediately determine if the used oil has been excessively thinned or thickened, thus rendering it unfit for further use.

It is to be noted that the method or apparatus of the present invention is truly portable, requires no electricity or electronics, and can be operated by untrained personnel. The limits of oil thinning and thickening can be determined by the individual user, and the holes 24, 25, and 26 in the bottom of the cups can be sized accordingly. Once the hole sizes have been established, the comparator 10 can be used for an indeterminate period of time. If the user changes either the thinned or thickened fluid limits, the hole sizes can be modified to give the desired results.

Also, the three cup, high-low viscosity comparator of the present invention can be used to compare high and low viscosity limits for any type of oil or fluid at any temperature.

In conclusion, the jar or container 27 contains used oil, the container 28 contains new oil or fluid, and the container 29 contains the same used oil or fluid. The cup 18 is for diluted oil or fluid, and the cup 20 is for thickened oil or fluid. The cup 19 is for the new oil or fluid. Thus, if the oil stops flowing from cup 18 before the oil stops flowing from cup 19, the oil is thinned. If the oil from cup 20 stops flowing after the oil from cup 19 stops flowing, the oil is thickened.

It is to be understood that in accordance with the present invention, the cups can be moved into and out of engagement with the containers, or the containers can be made so that they are movable to move into and out of engagement with the cups so that both concepts are encompassed by the present invention.

The number of cups and containers can be varied so that the present invention is not limited to three cups or containers. Also, the present invention is not limited to cups since tubes and the like can be used. The present invention tests shear rates. The present invention uses no electricity and glassware, and the apparatus is easy to clean.

The following is an explanation of use to conduct the high-low viscosity change test. This test determines both the reduction in viscosity of used oil caused by 2% dilution of fuel or thin oil added by mistake and a 40% increase in viscosity of used oil caused by oxidation, polymerization, or contamination.

It is to be understood that the conduct of the test is specifically to detect −2% thinning (dilution) and +40% thickening; however, this is only a sample of its use. The two limits can be changed to whatever the user desires.

The high-low viscosity comparator method of the present invention compares the rate of shear of a used oil against the rate of shear of the new oil. The high-low viscosity comparator works as follows:

1. Fill center jar (new oil) with the same new oil used in the engine and place the jar in the center of the sliding shelf.
2. Fill the end jars (used oil) with used oil from the engine and place on either end of the sliding shelf.
3. Allow all three oils to attain the same temperature as determined by the thermometer.
4. Place the triple high-low viscosity cups of the present invention on a hook over the center sliding shelf with the printing (−2%, new, and +40%) facing the operator. It is to be understood that such a shelf and cups and jars may be utilized or provided in a suitable test kit having various conventional accessories therein.
5. Bring the sliding shelf up so all the three cups are submerged in the respective oils in the three jars.
6. Lower the shelf and watch the flow of oil from the bottom of the three cups.

Regarding the results, if the oil from the new oil cup stops flowing first, the used oil is not diluted 2% or more, but the oil is thickened 40% or more.

If the oil in the −2% cup tops flowing before the new oil cup, the used oil more.

If the oil in the +40% cup stops flowing after the new oil, the used oil is thickened 40% or more.

At least two tests should be conducted on each used oil sample until duplicate tests are obtained. The cups should be wiped out with absorbent materials and be immediately ready for the next test. The high-low viscosity comparator of the present invention is made from a corrosion free, shock resistant, rugged material and should give a lifetime of use if not abused.

While several embodiments of the present invention have been illustrated herein in particular detail, it will be understood that variations and modifications may be effected without department from the spirit and scope of the novel concepts of this invention.

I claim:

1. In a high-low viscosity comparator, first, second, and third containers having a quantity of used fluid, new fluid, and used fluid therein, first, second, and third cups mounted for movement into and out of engagement with the containers, there being openings in the bottoms of said cups, the opening in the second cup being of greater size than the opening in the first cup and the opening in the third cup being of greater size than the opening in the second cup.

2. The structure as defined in claim 1 wherein said openings constitute means for visually determining viscosity properties of said used fluid, whereby if the fluid in the first cup stops flowing before the fluid in the second cup, the fluid is thinned, and if the fluid in the third cup stops flowing after the fluid in the second cup, the fluid is thickened.

3. In a high-low viscosity comparator for fluids, such as oil, a vertically disposed support member having a track therein, a body member including a vertically disposed element for engaging said track whereby said body member can move vertically up and down, a horizontally disposed cross piece integral with said vertically disposed element; first, second, and third spaced parallel arms depending from said cross piece, first second, and third cups affixed to the lower ends of said arms, there being holes in the bottom of said cups, said holes being of different sizes, and containers for selectively receiving said cups, said containers having fluids, such as oil, therein.

4. The structure as defined in claim 3 wherein each of said cups has an open top, an upper cylindrical portion, and a rounded bottom portion.

5. The structure as defined in claim 3 wherein the diameter of the holes increases so that the first cup has a predetermined size of hole, the second cup has a larger sized hole, and the third cup has a hole greater in size than the second cup.

6. A method for determining both decreases and increases in viscosity of used fluids, such as oils and to detect changes in the fluids during operation of equipment or when in storage comprising the steps of providing the same used fluid in first and third containers,
providing new fluid in a second container,
providing an apertured cup for each container, the apertures in said cups being of different sizes,
moving each of said apertured cups into a respective container to fill the cups with said fluids,
then raising the cups out of said containers to permit the fluids in said cups to discharge therefrom.

7. The method as defined in claim 6 wherein the hole in said second cup is of greater size than the hole in the first cup, and the hole in the third cup being of greater size than the hole in the second cup.

8. The method of claim 6, and wherein the step of raising said cups out of said containers comprises raising said cups simultaneously.

9. A viscosity comparator for fluids, comprising means for holding a fluid to be tested; means for holding a reference fluid, and means in each of said holding means for discharging said fluids from their respective holding means at different rates, said discharging means for each said holding means comprising a uniquely sized opening.

10. The viscosity comparator of claim 9, wherein said discharging means in each of said holding means is located in a bottom portion thereof.

11. The viscosity comparator of claim 9, and further including means for simultaneously filling each said holding means with its respective fluid.

12. The viscosity comparator of claim 9, and further including means for supporting said holding means at the same height, and means, slidably engagable with said supporting means, for permitting movement of each of said holding means into and out of reservoirs of the respective fluids, whereby each of said respective holding means may be filled with a respective fluid and then raised to permit the fluids to be discharged therefrom so that a viscosity comparison may be performed.

13. The viscosity comparator of claim 9, wherein the number of means for holding a fluid to be tested is greater than the number of means for holding the reference fluid.

14. A viscosity comparator for fluids, comprising:
first means for holding a first fluid;
second means for holding a second fluid;
apertured means, in each of said first and second holding means, for discharging said fluids therefrom;
said apertured discharging means in said first holding means being of a size different from the size of said apertured discharging means in said second holding means,
whereby when said fluids possess different viscosities, they are discharged from their respective holding means at different rates.

* * * * *